United States Patent
Harada

(10) Patent No.: US 7,623,289 B2
(45) Date of Patent: Nov. 24, 2009

(54) OBSERVATION APPARATUS HAVING THERMOREGULATION MECHANISM

(75) Inventor: Mitsuo Harada, Hachioji (JP)

(73) Assignee: Olympus Corporation, Tokyo (JP)

( * ) Notice: Subject to any disclaimer, the term of this patent is extended or adjusted under 35 U.S.C. 154(b) by 299 days.

(21) Appl. No.: 11/658,132

(22) PCT Filed: Jul. 21, 2005

(86) PCT No.: PCT/JP2005/013401
§ 371 (c)(1),
(2), (4) Date: Feb. 26, 2007

(87) PCT Pub. No.: WO2006/009212
PCT Pub. Date: Jan. 26, 2006

(65) Prior Publication Data
US 2007/0291354 A1     Dec. 20, 2007

(30) Foreign Application Priority Data
Jul. 22, 2004    (JP) .............................. 2004-214677

(51) Int. Cl.
*G02B 21/26*    (2006.01)
(52) U.S. Cl. .................................... 359/395
(58) Field of Classification Search ............... 359/368, 359/395, 665
See application file for complete search history.

(56) References Cited

U.S. PATENT DOCUMENTS 5,343,018 A * 8/1994 Limbach ...................... 219/200
5,410,429 A * 4/1995 Focht ........................... 359/395

FOREIGN PATENT DOCUMENTS

| JP | 3-25598 | 3/1991 |
| JP | 3-20810 | 5/1991 |
| JP | 7-36118 | 7/1995 |
| JP | 10-303114 | 11/1998 |
| JP | 2004-70307 | 3/2004 |

* cited by examiner

*Primary Examiner*—Alessandro Amari
(74) *Attorney, Agent, or Firm*—Scully, Scott, Murphy & Presser, P.C.

(57) ABSTRACT

An observation apparatus comprises a thermoregulation mechanism including a liquid receiving frame (28) that has a heater (43) for heating the outer frame of an immersion objective lens (13) and adapted to heat and maintain the temperature of the immersion liquid (30) contained in the frame (28) by means of the heater (43) and via the outer frame of the immersion objective lens (13) so as to maintain the temperature of the specimen (34) in the container at a constant level by utilizing heat conduction. The thermoregulation mechanism of the observation apparatus is so adapted that, when the temperature of the immersion liquid (30) decreases during a measurement/observation operation due to discharge of heat, the liquid (30) is heated again by the heater (43) to prevent the temperature of the specimen (34) from changing and maintain the temperature at a constant level.

12 Claims, 5 Drawing Sheets

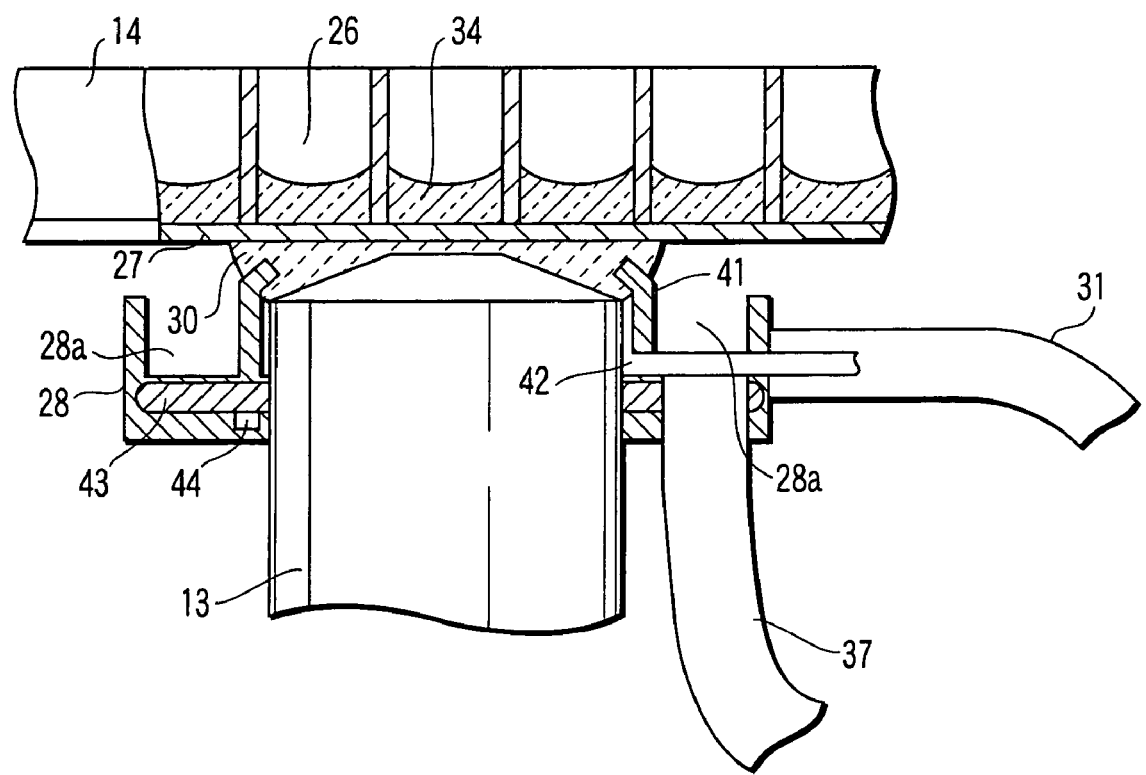
F I G. 2

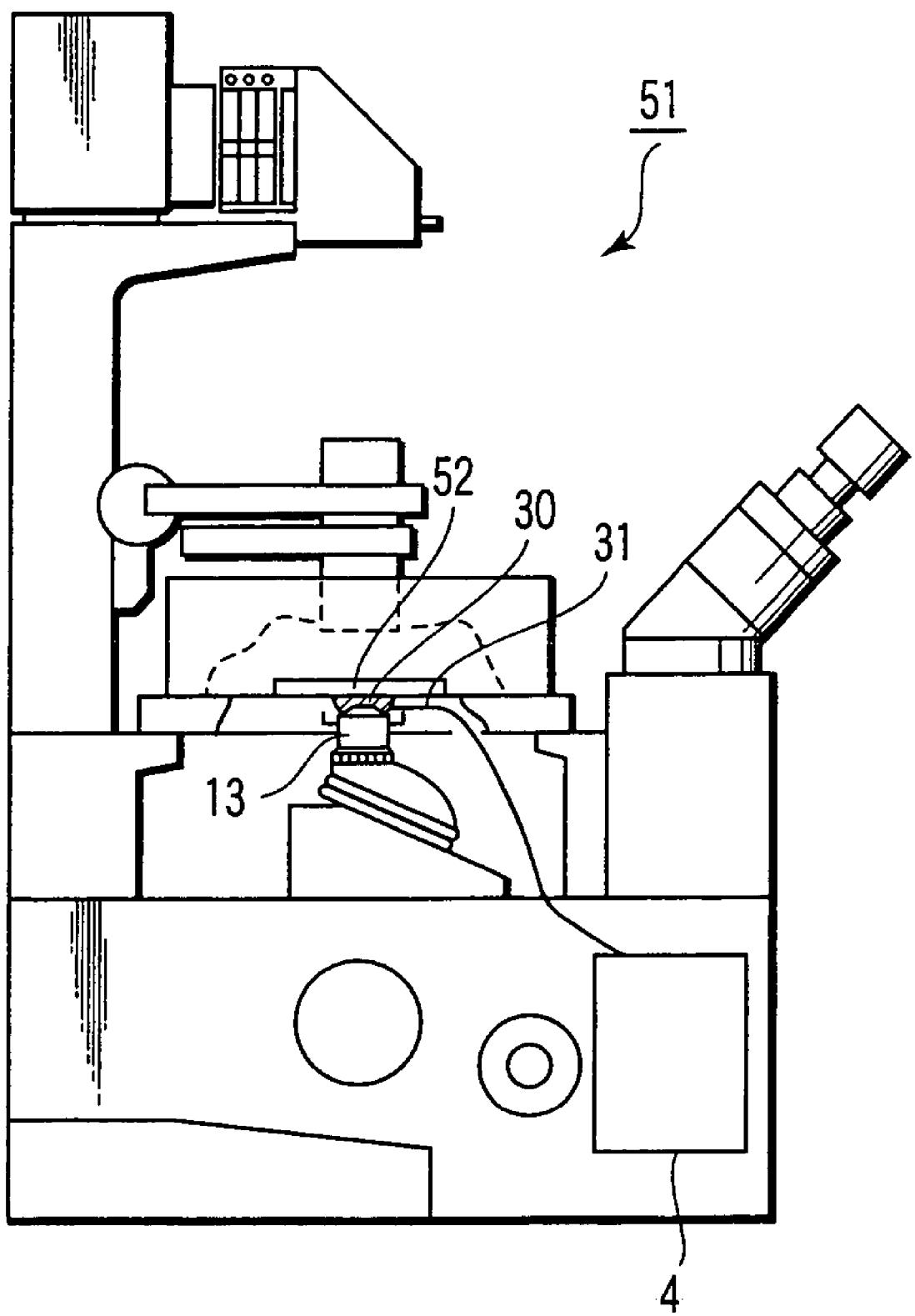
F I G. 3

OBSERVATION APPARATUS HAVING THERMOREGULATION MECHANISM

CROSS-REFERENCE

This application is a U.S. national phase application under 35 U.S.C. § 371 of International Application No. PCT/JP2005/013401 (not published in English), filed on Jul. 21, 2005, the entire content of which is incorporated herein by its reference.

TECHNICAL FIELD

This invention relates to an observation apparatus having a thermoregulation mechanism for the liquid containing an object of observation. Such an observation apparatus can suitably be used for an optical analyzer or a microscope.

BACKGROUND ART

Generally, when observing molecules floating in a liquid specimen with an observation apparatus such as a microscope, the temperature of the solution is preferably held to a constant level for observation because the motion of molecule is influenced by a temperature change of the solution. Various thermoregulation mechanisms have been proposed to date to keep the temperature of solution to a constant level.

For instance, Jpn. U.M. Appln. Publication No. 60-156521 discloses a microscope equipped with a table provided with a thermoregulation apparatus comprising a heat emitting section for heating the container of the specimen. Jpn. U.M. Appln. Publication No. 3-25598 discloses a culturing device to be used for a microscope by heating the culture/observation container in a heat retaining box and preventing steam from condensing in the heat retaining box by heating air surrounding the culture/observation container by means of a hot air blowing fan. Jpn. U.M. Appln. Publication No. 7-36118 discloses a microscope adapted to keep the temperature of the object of observation to a constant level by means of an arrangement for retaining the heat of the immersion objective lens itself by circulating heat retaining liquid in the immersion lens frame.

DISCLOSURE OF INVENTION

As pointed out above, when observing molecules floating in a liquid specimen and the objective lens is immersed in liquid, the temperature of the liquid specimen fluctuates as it is affected by the temperature of the objective lens itself. However, the heat retaining arrangements disclosed in Jpn. U.M. Appln. Publication No. 60-156521 and Jpn. U.M. Appln. Publication No. 3-25593 are realized without considering the movement of heat via an objective lens and hence they are not satisfactory for accurately retaining heat and regulating the temperature of the object of observation particularly when the specimen is observed via an immersion objective lens.

The arrangement described in Jpn. U.M. Appln. Publication No. 7-36118 requires the immersion objective lens to be provided with a passageway for supplying circulating liquid for the purpose of retaining heat. Then, a large outer frame needs to be used for the immersion objective lens to give rise to a problem of difficulty in terms of assembly, maintenance and the operation of adjusting the focal position.

In view of the above-identified circumstances, it is therefore the object of the present invention to provide an observation apparatus having a temperature regulation mechanism that can accurately retain the heat and regulate the temperature of the object of observation.

In an aspect of the present invention, the above object is achieved by providing an observation apparatus having an optical analysis feature of receiving light entering an immersion objective lens from an object of observation in liquid and a thermoregulation mechanism for the object of observation, the thermoregulation mechanism comprising: a liquid receiving frame adapted to be fitted to the outer periphery of the immersion objective lens and provided with a liquid holding wall for holding immersion liquid supplied to immerse the immersion objective lens; and a heating device adapted to be fitted to the liquid receiving frame to heat the outer frame of the immersion objective lens.

In another aspect of the present invention, there is provided an observation apparatus having a microscope feature of receiving light entering an immersion objective lens from an object of observation in liquid and a thermoregulation mechanism for the object of observation, the thermoregulation mechanism comprising: a liquid receiving frame adapted to be fitted to the outer periphery of the immersion objective lens and provided with a liquid holding wall for holding immersion liquid supplied to immerse the immersion objective lens; and a heating device adapted to be fitted to the liquid receiving frame to heat the outer frame of the immersion objective lens.

BRIEF DESCRIPTION OF DRAWINGS

FIG. 2 is a schematic detailed cross-sectional view of the liquid receiving frame of the optical analyzer of FIG. 1;

FIG. 3 is an inverted-type microscope that is the second embodiment of observation apparatus having a thermoregulation mechanism according to the present invention, showing the configuration thereof;

BEST MODE FOR CARRYING OUT THE INVENTION

Now, the present invention will be described in greater detail by referring to the accompanying drawings that illustrate preferred embodiments of the invention.

Figure 1:
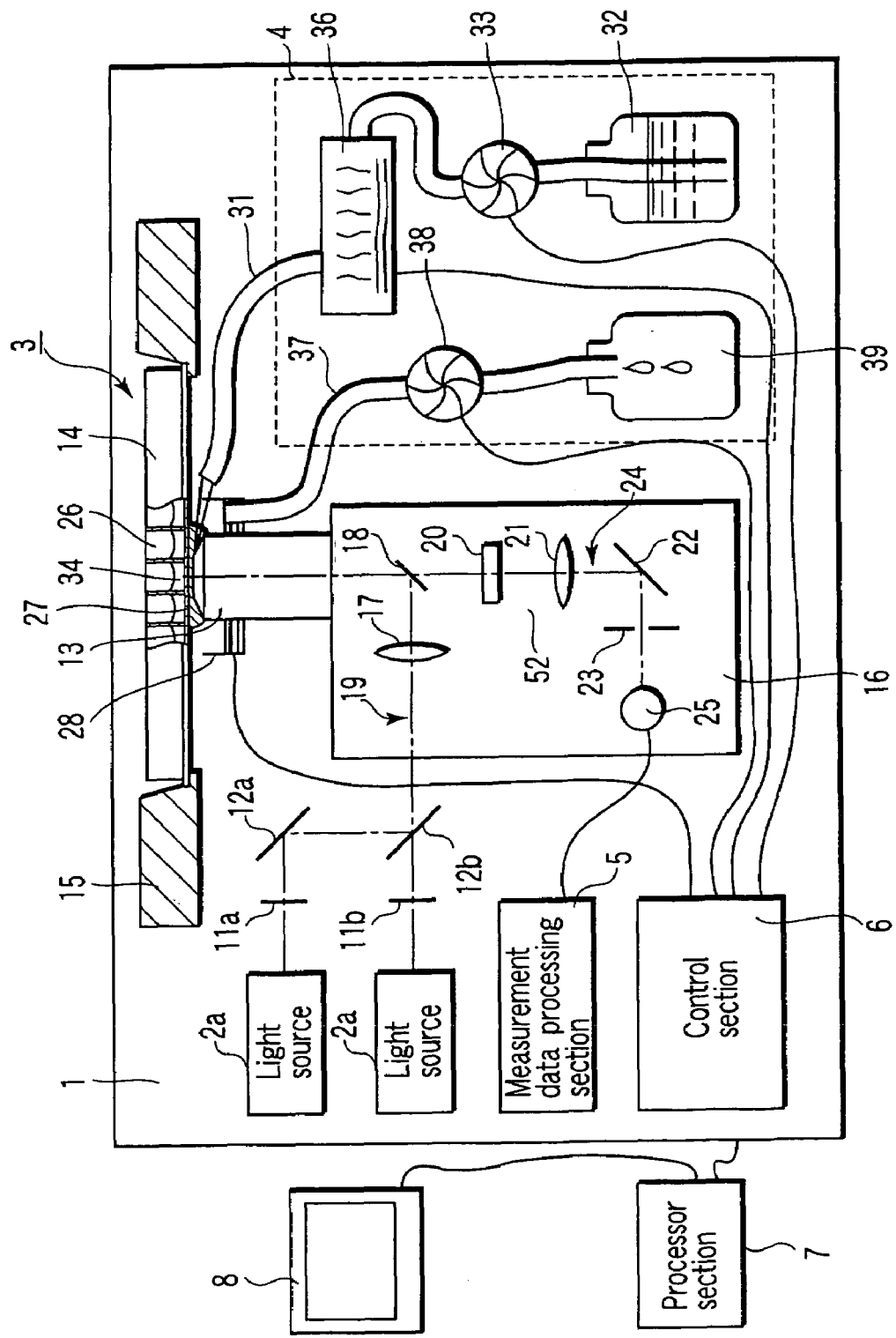
FIG. 1 is a schematic illustration of the optical analyzer that is the first embodiment of observation apparatus having a thermoregulation mechanism according to the present invention, showing the configuration thereof.

FIG. 1 is a schematic illustration of the optical analyzer that is the first embodiment of observation apparatus (optical analyzer) having a thermoregulation mechanism according to the present invention, showing the configuration thereof. FIG. 2 is a schematic detailed cross-sectional view of the liquid receiving frame of the optical analyzer of FIG. 1.

The optical analyzer 1 comprises as major components thereof two light sources 2a, 2b, an inverted-type fluorescent microscope 3, a liquid supply/collection unit 4, a measurement data processing section 5 and a control section 6 and is externally provided with a personal computer that operates as a processor section 7 and a display section 8.

The light sources 2a, 2b are typically a laser beam generator and the laser beams emitted from the light sources 2a, 2b are combined and made to enter the inverted-type fluorescent microscope 3 via an optical path formed by filters 11a, 11b, a mirror 12a and a dichroic mirror 12b.

The inverted-type microscope 3 includes an immersion objective lens 13, a stage 15 supporting a micro-plate 14 and a confocal optical system 16. The confocal optical system 16 leads the combined laser beams to the immersion objective lens 13 via an optical path 19 formed by a lens 17 and a dichroic mirror 18. On the other hand, the measuring light from the immersion objective lens 13 are led to a photo-electric signal converter 25 via an optical path 24 formed by the dichroic mirror 18, an absorption filter 20, a lens 21, a mirror 22 and a pin hole section 23 so that the fluorescent light emitted from the object of observation that is marked by fluorescent light is converted into a measurement signal (video data). The measurement signal is then output to the measurement data processing section 5 and turned into a data, which data is then output to the processor section 7. The photo-electric signal converter 25 is typically formed by using a photo multiplier or an avalanche photodiode. The processor section 7 determines the characteristics of the object of observation according to the measurement data and executes an imaging process so as to have the display section 8 display the produced image along with various other processes and data recording operations.

A micro-plate 14 is arranged above the immersion objective lens 13 and supported by the stage 15. The stage, or table, 15 can move the micro-plate 14 in planar directions perpendicular to the optical axis. A plurality of wells 26 is formed in the micro-plate 14 to contain the object of observation (or the specimen). A transparent cover glass 27 is arranged at the bottom side of the wells 26 to allow the laser beams emitted from the light sources 2a, 2b to be transmitted. A liquid receiving frame 28 is fitted to the outer periphery of the immersion objective lens 13 at a position close to the front end thereof. The liquid receiving frame 28 operates to prevent the immersion liquid 30 from flowing into small parts of the immersion objective lens 13 and the units located below it.

The liquid supply/collection unit 4 supplies immersion liquid between the immersion objective lens 13 and the micro-plate 14. The liquid supply/collection unit 4 includes an immersion liquid supply system and an immersion liquid collection system. Of these systems, firstly the supply system has a supply nozzle 31 for supplying immersion liquid 30 (shown in FIG. 2) between the cover glass 27 of the micro-plate 14 and the immersion objective lens 13, a supply bottle 32 for containing immersion liquid 30, a pump 33 for feeding immersion liquid 30 from the supply bottle 32 to the supply nozzle 31 and a heating unit 36 for heating the immersion liquid 30 being supplied to the temperature level same as that of the object of observation 34. On the other hand, the collection system has a discharge nozzle 37 for discharging immersion liquid 30 from the liquid receiving frame 28, a discharge pump 38 for sucking immersion liquid 30 from the discharge nozzle 37 and a waste bottle 39 for collecting the discharged immersion liquid 30.

FIG. 2 is a schematic detailed cross-sectional view of the above-described liquid receiving frame 28. Note, however, that the pump 33 may be omitted so that the operator may manually supply immersion liquid.

A liquid holding wall 41 is arranged in the inside of the liquid receiving frame 28 so as to run along the outer frame of the immersion objective lens 13 when mounted. The liquid holding wall 41 stably holds the immersion liquid 30 between the immersion objective lens 13 and the over glass 27.

The supply port 42 of immersion liquid 30 is arranged in the inside of the liquid holding wall 41. The immersion liquid 30 supplied from the supply port 42 to the inside of the liquid holding wall 41 fills the gap between the immersion objective lens 13 and the cover glass 27. The immersion liquid 30 that spills to the outside of the liquid holding wall 41 falls into the groove 28a of the liquid receiving frame 28 of immersion liquid 30 and collected in the waste bottle 39 via the discharge nozzle 37.

Additionally, a heater 43 is arranged in the liquid receiving frame 28 and held in contact with the outer frame of the immersion objective lens 13 to heat the immersion objective lens 13. No thermal fluctuations take place in the object of observation 34 when the immersion objective lens 13 is heated and held to the temperature level same as that of the object of observation 34 by means of the heater 43 if the immersion objective lens 13 is immersed in the immersion liquid 30 whose temperature is same as that of the object of observation 34. Thus, it is possible to maintain the temperature of the object of observation 34 at a constant level.

When the temperature of the immersion liquid 30 is lower than that of the object of observation 34, it can be held to a constant level by heating the immersion liquid 30 by means of the heater 43 and raise the temperature of the immersion liquid 30 to that of the object of observation 34 via the outer frame of the immersion objective lens 13. If such is the case, the control section 6 regulates the temperature of the heater 43 and that of the heating unit 36 according to the temperature information from the sensor 44 arranged at the liquid receiving frame 28 and a sensor (not shown) arranged at the heating unit 36 so as to make the immersion liquid 30 show a temperature level same as that of the object of observation 34.

As described above, with this embodiment, it is possible to prevent the heat of the immersion liquid 30 from moving, if partly, to the immersion objective lens 13 by heating the immersion objective lens 13 by means of the heater 43 of the liquid receiving frame 28 or it is possible to heat the immersion liquid 30 via the immersion objective lens 13. Thus, it is possible to accurately maintain and regulate the temperature of the object of observation.

The supply nozzle 31, the discharge nozzle 37, the liquid holding wall 41 and the heater 43 are integrally formed with the liquid receiving frame 28. Therefore, they can be removably fitted to the immersion objective lens 13 with ease. Thus, they can be replaced or serviced with ease. Additionally, since the liquid recording frame 28 is adapted to be fitted to the front end part of the immersion objective lens 13, the focusing operation can be conducted with ease without obstructing any movement of the immersion liquid objective lens 13 in the axial direction.

The temperature of the immersion liquid 30 is maintained and regulated via the immersion objective lens 13 that is heated by the heater 43 in this embodiment. However, the liquid holding wall 41 may be formed by using a thermally highly conductive material so that it conveys the heat, if partly, generated by the heater 43 to the immersion liquid 30 so as to regulate the temperature of the immersion liquid 30.

FIG. 3 is an apparatus having a microscope feature (e.g., inverted-type microscope) that is the second embodiment of observation apparatus having a thermoregulation mechanism according to the present invention, showing the configuration thereof. A thermoregulation mechanism according to the present invention can be applied to the inverted-type microscope 51 when the latter is used to observe an object of observation by using a glass dish 52. Like the above-described embodiment, immersion liquid 30 is supplied between the dish 52 and the immersion objective lens 13 to maintain and regulate the temperature of the immersion liquid 30 by means of a heater (the heater 43 in FIG. 2). Note, however, that the pump 33 may be omitted so that the operator may manually supply immersion liquid.

While an inverted-type microscope 51 is used as an observation apparatus of the above-described embodiment, this embodiment of thermoregulation mechanism can be applied to an erect microscope employing an immersion objective lens. If such is the case, the liquid receiving frame 29 does not operate but the temperature of the specimen can be maintained and regulated by heating the immersion objective lens by means of the heater 43 as in the case of this embodiment.

Figure 4A:
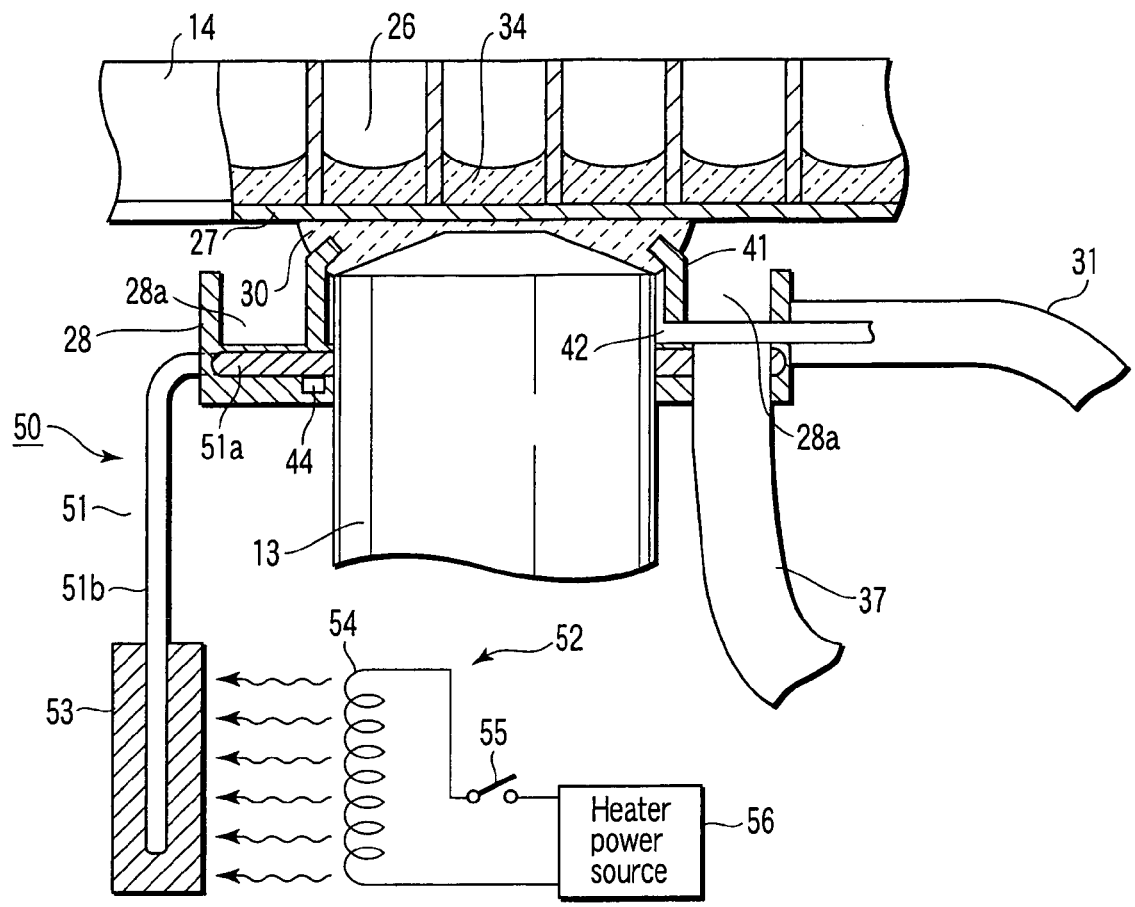
FIG. 4A is a schematic illustration of the heater of the thermoregulation mechanism of the first and second embodiments, showing the first feasible configuration.

FIG. 4A is a schematic illustration of the heater of the thermoregulation mechanism of the above-described first and second embodiments, showing the first feasible configuration.

With the first feasible configuration, the above-described heater 43 integrally formed in the liquid receiving frame 28 is replaced by a heating unit 50 including a heater section 51 having a heat moving member and a heat supply section 52 that is a member independent from the heater section 51 and arranged close to the heat moving member to supply heat.

The heater section 51 includes a thermal conductor section 51a mounted in the liquid receiving frame 28 like the heater 43, a heat moving member 51b for leading heat to the outside and a heat receiving body 53 arranged at the external end of the heat moving member 51b. The thermal conductor section 51a and the heat moving member 51b are filled in the inside thereof with a heat pipe and circulating liquid so as to produce circulation of heat in the entire inside so that the heat supplied to the heat moving member 51b from the outside is conducted, if partly, to the object of observation 34 via the heat conductor section 51a.

The heat supply section 52 includes a heat emission heater 54 for supplying heat to the heat receiving body 53 and a heater power source 56 connected to the heater section 51 via a switch 55. The heat emission heater 54 may be a heating wire heater such as a nickel-chrome wire heater, a ceramic heater or an infrared heater.

With the above-described arrangement, the heat emission heater 54 is placed close to the heat receiving body 53 of the heat moving member 51b for leading heat to the outside from the liquid receiving frame 28. The regulated output from the heater power source 56 is supplied to the heat emission heater 54, which then emits heat at a controlled heat supply rate. The heat receiving body 53 that receives the supply of heat then conveys the generated heat to the object of observation 34 via the heat moving member 51b and the heat conductor section 51a.

Figure 4B:
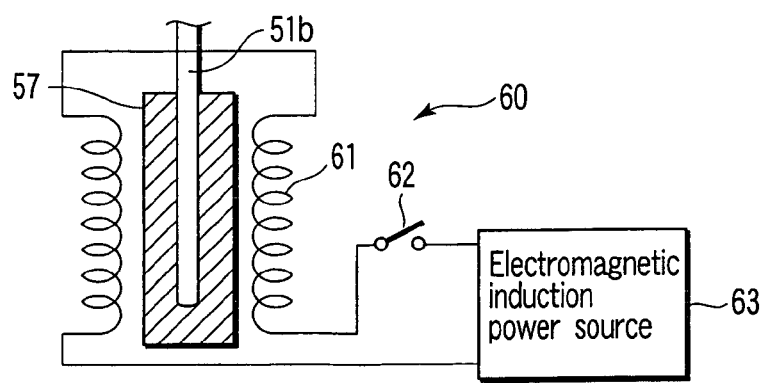
FIG. 4B is a schematic illustration of a heater obtained by modifying the heater of the thermoregulation mechanism of the first and second embodiments, showing the modified first feasible configuration.

Besides the above-described arrangements, it is also possible to use a heat supply section 60 formed by using an electromagnetic induction body as shown in FIG. 4B. The electromagnetic induction body (IH) 61 is placed close to the heat receiving body 57. The electromagnetic induction body (IH) 61 is connected to an electromagnetic induction power source 63 via a switch 62. The electromagnetic induction generated by the electromagnetic induction power source 63 is supplied from the electromagnetic induction body (IH) 61 to the heat receiving body 57. The heat receiving body 57 is made of a magnetic material and conveys the heat, if partly, generated by the received electromagnetic induction to the object of observation 34. With the arrangement of FIG. 4B that utilizes electromagnetic induction is particularly advantageous for a situation of observation where the space facing the object is narrow and limited.

Figure 5:
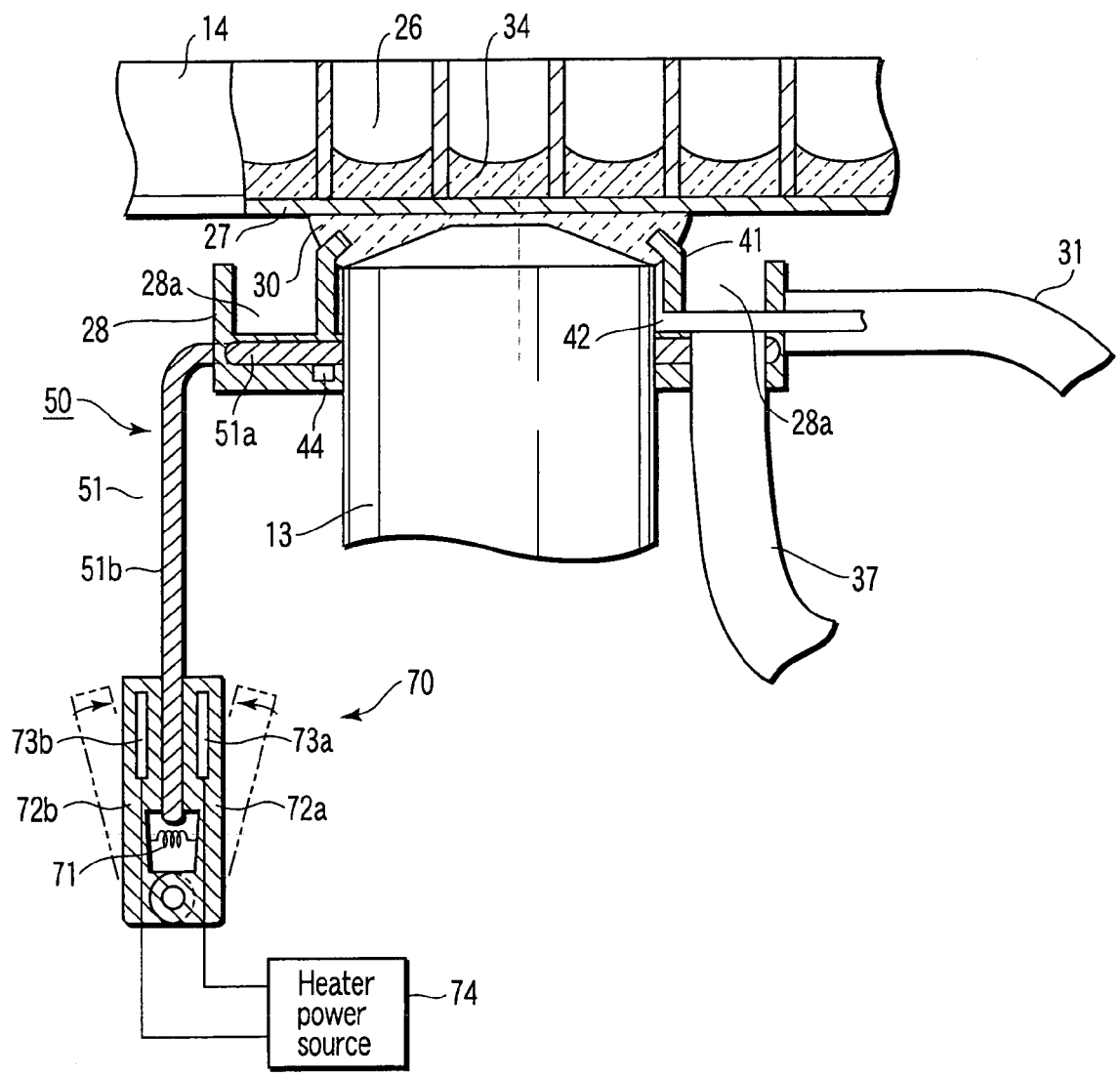
FIG. 5 is a schematic illustration of the heater of the thermoregulation mechanism of the first and second embodiments, showing the second feasible configuration.

FIG. 5 is a schematic illustration of the heater of the thermoregulation mechanism of the first and second embodiments, showing the second feasible configuration, where the heating unit is removably mountable and the temperature thereof is controllable.

With this arrangement, the heat conductor section 51a of the heater section 51 of the above-described first feasible configuration is mounted in the liquid receiving frame 28 and heat is supplied from the outside by means of a heat supply section 70 that is removably mountable on the heat moving member 51b led out to the outside from the inside of the liquid receiving frame 28.

The heat supply section 70 is fitted so as to pinch the heat conductor moving member 51b that is led out to the outside so as to be held in tight contact with the heat moving member 51b. The heat supply section 70 is independent from the heat moving member 51b and made to show a forceps-like (or clip-like) profile. It is urged by a resilient member 71 such as a coil spring. At least heater members 73a, 73b that can regulate temperature are contained respectively in their jaw sections 72a, 72b and connected to a heater power source 74 so that a desired temperature can be supplied to the heat conductor member.

As the heat supply section 70 is made to be removably mountable and arranged so as to pinch the heat moving member 51b between the two jaw sections 72a, 72b thereof, the operation of inspecting them can be conducted with ease and they can be replaced with ease. With this arrangement, the temperature of the object of observation can be regulated efficiently because the temperature of the supplied liquid is regulated not only before the supply but also at a position close to the object of observation 34.

The observation apparatus equipped with a thermoregulation mechanism according to the present invention provides the following advantages.

First, the outer frame of the immersion objective lens is heated to the temperature level same as that of the specimen (liquid) by means of a heater and the immersion objective lens is immersed into the immersion liquid. Thus, heat is not moved from the immersion liquid to the immersion objective lens or vice versa to prevent a measurement error from taking place due to thermal fluctuations of the specimen.

Second, when the temperature of the immersion liquid is lower than that of the object, it is possible to supply heat to the immersion liquid from a heating unit via the outer frame of the immersion objective lens. Thus, it is possible to maintain the temperature of the object in the container during the observation.

Third, the liquid receiving frame and the heating unit are integrally formed so that the liquid receiving frame and the immersion objective lens can be assembled and serviced with ease. Additionally, the immersion objective lens can be operated with ease.

Fourth, the heater section and the heating unit are made independent from each other so as to make it removably mountable. Thus, the operation of thermoregulation can be conducted from the outside. Additionally, the use of electromagnetic induction is particularly advantageous for a situation of observation where the space facing the object is narrow and limited.

Fifth, a liquid supply unit is arranged between the immersion objective lens and the container to supply immersion liquid and a liquid heating unit is provided to heat the immersion liquid supplied from the liquid supply unit. With this arrangement, it is possible to supply immersion liquid heated by the heating unit between the immersion objective lens and the container to maintain the temperature of the specimen in the container. The specimen may be heated indirectly by the heating unit by way a liquid holding wall.

While embodiments of observation apparatus having a thermoregulation mechanism according to the present invention are described above in terms of an optical analysis feature and a microscope feature (inverted-type fluorescent microscope, inverted-type microscope and erect microscope), the present invention is by no means limited thereto and equally applicable to any similar apparatus so long as such apparatus are adapted to observation of a specimen via an immersion objective lens. Additionally, if desired, components of any of the above-described embodiments may be combined appropriately and/or omitted.

The invention claimed is:

1. An observation apparatus having an optical analysis feature of receiving light entering an immersion objective lens from an object of observation in liquid and a thermoregulation mechanism for the object of observation, comprising:
   a liquid receiving frame adapted to be fitted to the outer periphery of the immersion objective lens and provided with a liquid holding wall for holding immersion liquid supplied to immerse the immersion objective lens; and
   a heating device adapted to be fitted to the liquid receiving frame to heat the outer frame of the immersion objective lens;
   wherein the heating device includes:
   a heater section having a heat conveying section mounted in the liquid receiving frame, a heat moving member communicating with the heat conveying section and led out from the liquid receiving frame to the outside and a heat receiving body arranged at an end of the heat moving member; and
   a heat supply section having a heat emission heater arranged close to the heat receiving body of the heater section to supply heat to the heat receiving body and a heater power source for controlling the heat emission rate of the heat emission heater.

2. The apparatus according to claim 1, wherein the heating device is integrally fitted to the liquid receiving frame.

3. The apparatus according to claim 1, further comprising:
   a liquid supply unit for supplying immersion liquid so as to be held by the liquid holding wall between the immersion objective lens and the liquid receiving frame;
   the liquid supply unit having a liquid heating device for heating the immersion liquid before being supplied to the liquid receiving frame.

4. The apparatus according to claim 1, wherein the heating device is adapted to heat the outer frame of the immersion objective lens and heat and hold the temperature of the liquid holding wall.

5. An observation apparatus having an optical analysis feature of receiving light entering an immersion objective lens from an object of observation in liquid and a thermoregulation mechanism for the object of observation, comprising:
   a liquid receiving frame adapted to be fitted to the outer periphery of the immersion objective lens and provided with a liquid holding wall for holding immersion liquid supplied to immerse the immersion objective lens; and
   a heating device adapted to be fitted to the liquid receiving frame to heat the outer frame of the immersion objective lens;
   wherein the heating device includes:
   a heater section having a heat conveying section mounted in the liquid receiving frame, a heat moving member communicating with the heat conveying section and led out from the liquid receiving frame to the outside and a heat receiving body made of a magnetic body; and
   a heat supply section having an electromagnetic induction body arranged close to the heat receiving body of the heater section to supply electromagnetic induction to the heat receiving body and an electromagnetic induction power source for causing the electromagnetic induction body to generate electromagnetic induction.

6. The apparatus according to claim 5, wherein the heating device is integrally fitted to the liquid receiving frame.

7. The apparatus according to claim 5, further comprising:
   a liquid supply unit for supplying immersion liquid so as to be held by the liquid holding wall between the immersion objective lens and the liquid receiving frame;
   the liquid supply unit having a liquid heating device for heating the immersion liquid before being supplied to the liquid receiving frame.

8. The apparatus according to claim 5, wherein the heating device is adapted to heat the outer frame of the immersion objective lens and heat and hold the temperature of the liquid holding wall.

9. An observation apparatus having an optical analysis feature of receiving light entering an immersion objective lens from an object of observation in liquid and a thermoregulation mechanism for the object of observation, comprising:
   a liquid receiving frame adapted to be fitted to the outer periphery of the immersion objective lens and provided with a liquid holding wall for holding immersion liquid supplied to immerse the immersion objective lens; and
   a heating device adapted to be fitted to the liquid receiving frame to heat the outer frame of the immersion objective lens;
   wherein the heating device includes:
   a heater section having a heat conveying section mounted in the liquid receiving frame, a heat moving member communicating with the heat conveying section and led out from the liquid receiving frame to the outside and a heat receiving body arranged at an end of the heat moving member; and
   a heat supply section having two jaw sections pinching the heat receiving body, an urging member for urging the jaw sections to close, heater members arranged respectively in the jaw sections and a heater power source for controlling the temperature of the heater member to a desired temperature level.

10. The apparatus according to claim 9, wherein the heating device is integrally fitted to the liquid receiving frame.

11. The apparatus according to claim 9, further comprising:
    a liquid supply unit for supplying immersion liquid so as to be held by the liquid holding wall between the immersion objective lens and the liquid receiving frame;
    the liquid supply unit having a liquid heating device for heating the immersion liquid before being supplied to the liquid receiving frame.

12. The apparatus according to claim 9, wherein the heating device is adapted to heat the outer frame of the immersion objective lens and heat and hold the temperature of the liquid holding wall.

* * * * *